(12) United States Patent
Pepper et al.

(10) Patent No.: US 7,262,861 B1
(45) Date of Patent: Aug. 28, 2007

(54) ULTRASOUND SINGLE-ELEMENT NON-CONTACTING INSPECTION SYSTEM

(75) Inventors: David M. Pepper, Malibu, CA (US); Thomas R. O'Meara, Malibu, CA (US)

(73) Assignee: MRL Laboratories, LLC, Malibu, CA (US)

( * ) Notice: Subject to any disclaimer, the term of this patent is extended or adjusted under 35 U.S.C. 154(b) by 284 days.

(21) Appl. No.: 10/852,782

(22) Filed: May 24, 2004

(51) Int. Cl.
*G01B 11/02* (2006.01)
(52) U.S. Cl. .......................... 356/502; 73/655
(58) Field of Classification Search ............... 356/502, 356/432; 73/655, 657
See application file for complete search history.

(56) References Cited

U.S. PATENT DOCUMENTS

| | | | |
|---|---|---|---|
| 5,585,921 A | 12/1996 | Pepper et al. ............... 356/357 |
| 5,684,592 A | 11/1997 | Mitchell et al. ............ 356/357 |
| 5,909,279 A | 6/1999 | Pepper et al. ............... 356/345 |
| 6,008,887 A | 12/1999 | Klein et al. ................. 356/28.5 |
| 6,057,927 A | 5/2000 | Lévesque et al. ........ 356/432 T |
| 6,075,603 A | 6/2000 | O'Meara et al. ............ 356/358 |
| 6,087,652 A | 7/2000 | O'Meara et al. ......... 250/214.1 |
| 6,115,127 A | 9/2000 | Brodeur et al. ............. 356/357 |
| 6,285,514 B1 | 9/2001 | O'Meara et al. ............ 359/721 |
| 6,342,721 B1 | 1/2002 | Nolte et al. ................. 257/448 |

OTHER PUBLICATIONS

Fisher, D.J., et al., "Design and Manufacture of a Gradient-Index Axicon," *Applied Optics*, vol. 39, No. 16, pp. 2687-2694 (Jun. 1, 2000).
Murray, T.W., et al., "Adaptive Optical Array Receivers for Detection of Surface Acoustic Waves," *Applied Optics*, vol. 39, No. 19, pp. 3276-3284 (Jul. 1, 2000).
Scruby, C.B., et al., "Long-Path-Difference Interferometry," *Laser Ultrasonics, Techniques and Applications*, Section 3.10, pp. 123-127 (1990).
Scruby, C.B., et al., "Applications Using Laser Generation of Ultrasound," *Laser Ultrasonics, Techniques and Applications*, Section 6, pp. 325-351 (1990).

*Primary Examiner*—Hwa (Andrew) Lee
*Assistant Examiner*—Marissa J. Detschel
(74) *Attorney, Agent, or Firm*—Ladas & Parry

(57) ABSTRACT

A laser ultrasonic inspection apparatus and method which enables remote sensing of thickness, hardness, temperature and/or internal defect detection is disclosed. A laser generator impinges a workpiece with light for generating a thermoelastic acoustic reaction in a workpiece. A probe laser impinges the workpiece with an annularly-shaped probe light for interaction with the acoustic signal in the workpiece resulting in a modulated return beam. A photodetector having a sensitive region for detecting an annularly-shaped fringe pattern generated by an interaction of a reference signal and with the modulated return beam at said sensitive region.

26 Claims, 5 Drawing Sheets

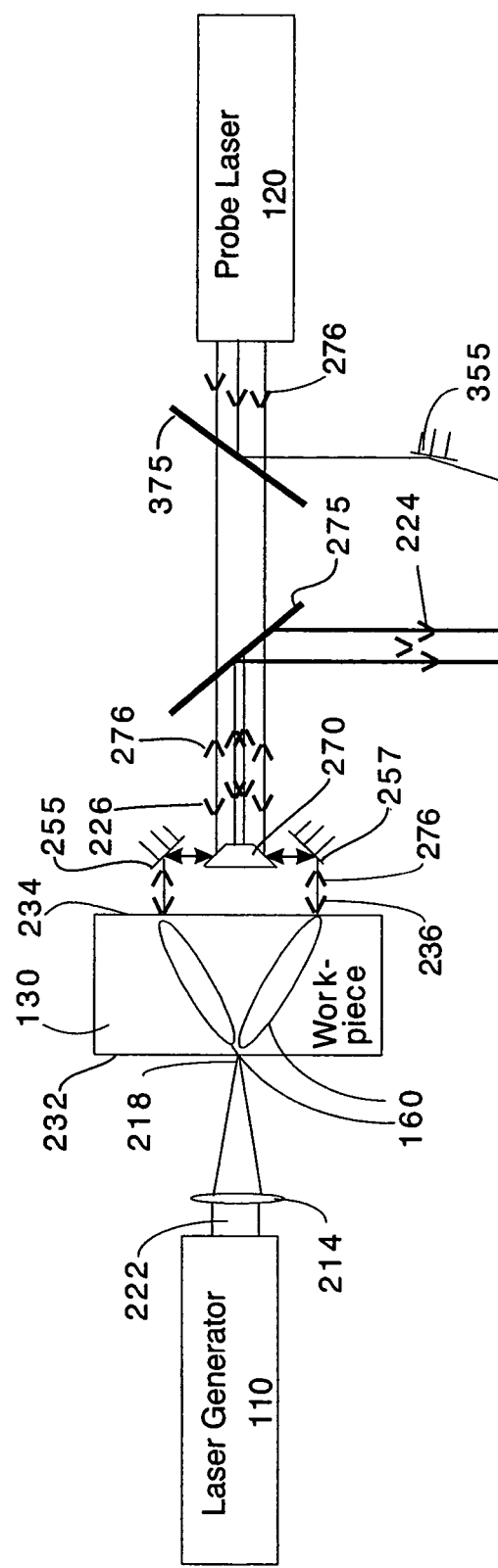
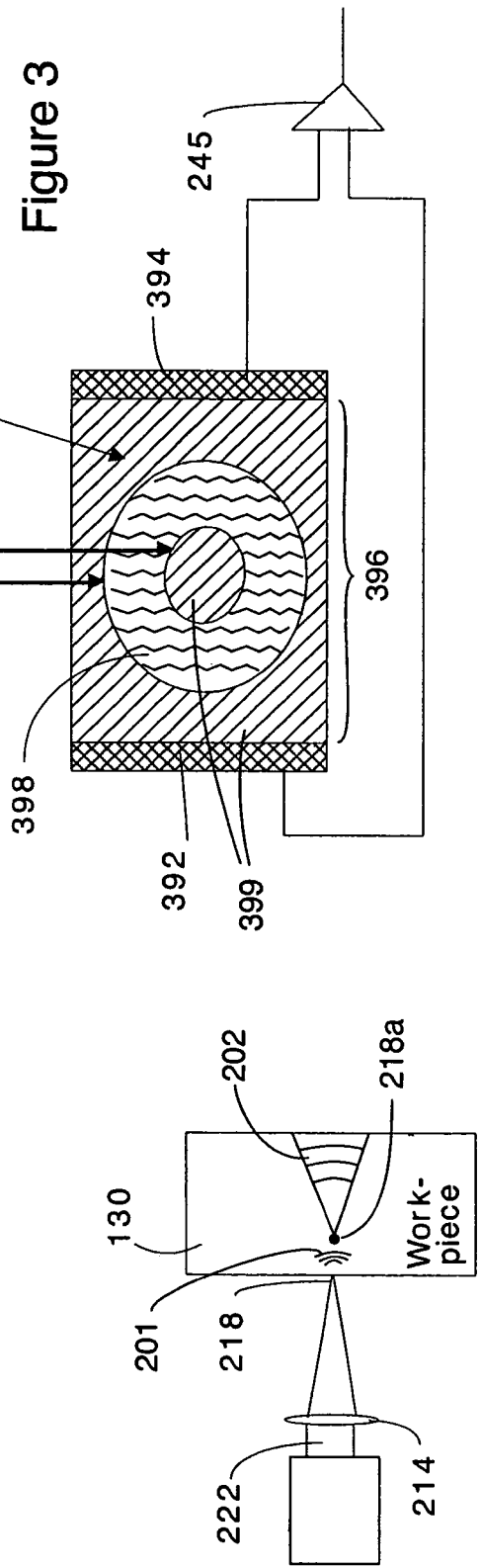
Figure 3
Figure 3a

ULTRASOUND SINGLE-ELEMENT NON-CONTACTING INSPECTION SYSTEM

BACKGROUND

1. Technical Field

The present disclosure relates generally to ultrasonic non-contacting inspection systems and more particularly to ultrasonic non-contacting inspection systems requiring only a single element sensor to realize high spatial resolution acoustic imagery in one embodiment, and spatially averaged probing of material properties in another embodiment

2. Description of Related Art

Ultrasonic waves are commonly used to probe a variety of materials (workpieces), particularly for thickness gauging and flaw detection. The sound waves have usually been generated with a contact piezoelectric transducer (PZT). The launched waves propagate through the material, reflecting from interfaces (in thickness gauging applications) or internal features (in flaw detection applications). The scattered sound propagates back to the surface of the workpiece, causing the surface to vibrate at the ultrasound frequency. This vibration has been previously detected with a contact PZT similar to the one used to generate the second.

Optical detection techniques, such as those described in C. B. Scruby and L. E. Drain, *Laser Ultrasonics, Techniques and Applications*, Adam Hilger, New York (1990), pages 325–350, can be used in place of the piezoelectric transducers to remotely detect the workpiece vibrations. Generally, a laser probe beam is directed onto the workpiece. When the surface vibrates it imparts a phase shift onto the reflected beam. This phase shift is detected with a photodetector after mixing the reflected probe beam with a stable reference beam and measuring the amplitude and frequency or phase of the detector output intensity fluctuations. The reference beam originates from the same laser source as the reflected probe beam, and the output signal from the photodetector or an electronic phase detector corresponds to the surface motion.

One problem with laser detection systems is low sensitivity. Typically, the workpiece surface that is being probed has a diffusely reflecting or scattering quality. Consequently, the reflected beam is highly aberrated and its wavefront is mismatched with respect to the reference beam. The aberrated, reflected beam produces a "speckle" field distribution on the optical detector that is used to detect the optical interference between the reflected and reference beams. The phase relationship between the reflected probe beam and the reference beam is maintained only over a single "speckle" diameter. Consequently, the phase relationship can be set optimally only for light within the speckle area; light within other speckles will have a different and generally non-optimal phase relationship with the reference beam. The resulting detector signal can thus be thousands of times weaker, due to multiple speckle capture, than would be the case if the surface were a perfect mirror (in which all light would be in a single speckle).

One prior interferometric technique for detecting ultrasound uses a "self-referencing" interferometer that produces an output proportional to a temporal difference vibration signal, rather than to the displacement, of the moving workpiece surface. Time delay interferometry, described in the Scruby et al. book, pages 123–127, is one such technique. In time delay interferometry the probe beam that is reflected from the workpiece surface is split into two interferometer beams and then recombined at a standard photodetector, with one of the beams time-delayed with respect to the other such as by having it traverse a longer distance. The two beams are collinear when they are recombined at the photodetector, and the light intensity at the photodetector is proportional to the velocity of the workpiece surface. Ideally, the reflected readout beam is interfered with a time-delayed replica of itself and the wavefronts of the two interfering beams are substantially matched. Consequently, a phase shift in one leg of the interferometer is common to all speckles, and all speckles can be detected optimally. Unlike a conventional interferometer, which has a flat frequency response to phase shifts, a time delay interferometer has a bandpass type of response. The time delay interferometer suppresses both the low frequency (below ultrasonic frequencies), as well as certain ultrasonic frequency vibrations.

In U.S. Pat. No. 5,585,921, for "Laser-Ultrasonic Non-Destructive, Non-Contacting Inspection System" by the present applicants and others, a phased-array contactless optical excitation and detection scheme is disclosed in which an array of acoustic waves are generated in the workpiece by a short pulse optical transmitter beam with a beam geometry that is tailored to focus the acoustic waves at an inspection site within the workpiece. The acoustic waves are then detected by reflecting an optical readout beam from a vibrating surface of the workpiece and optically interfering it with a reference beam. The readout beam geometry causes it to detect only those acoustic waves that arrive from the focal inspection site; other acoustic waves are out of phase with each other and cancel. The system employs relatively expensive electronic tracking hardware to compensate for large amplitude, low frequency whole body motions typical in an industrial environment. It uses optical summation for beam formation and thus requires path compensation via photorefractive wavefront compensators, which are relatively slow and introduce occasional signal dropouts.

Another U.S. patent by the present applicants and others, U.S. Pat. No. 5,684,592, for "System and Method for Detecting Ultrasound Using Timedelay Interferometry," discloses another contactless system in which an optical probe beam is again reflected and phase modulated by a workpiece surface that is vibrated by ultrasound. A timedelay interferometer optically interferes the phase modulated probe beam reflection with a time-delayed replica of itself to produce interference fringes that move in accordance with the workpiece surface displacement temporal differences. The fringes are detected by a non-steady-state photo-electromotive-force, or photo-EMF, detector that generates an output signal when the frequency of the fringe motion exceeds a given threshold. While this system is relatively insensitive to rough workpiece surfaces, suppresses low frequency noise and provides high sensitivity without the need for active stabilization, the delay lines require long, cumbersome optical fibers to form the beam with the attendant input-output coupling losses and power limiting nonlinear effects.

In U.S. Pat. No. 6,075,603, by the present applicants, for "Contactless Acoustic Sensing System With Detector Array Scanning and Self-Calibrating," another contactless system for imaging an acoustic source within a workpiece is disclosed. In this system, an array of discrete optical detectors are arranged in a pattern. A probe beam is directed onto a vibrating surface in a pattern that corresponds to the detector array. The probe beam is reflected onto the detector array and a reference beam is also directed onto the detector array at an angle to the probe beam to produce fringe patterns on the detectors that correspond to the surface vibration pattern. A readout system utilizes the discrete detector outputs to produce an array output signal indicative of at least a size and two dimensional location for the acoustic source relative to the vibrating surface. While this system allows for electronic beam steering and focusing, it includes arrays, which possess many discrete detector elements and associated circuitry. The contents of U.S. Pat. No. 6,075,603 is hereby incorporated herein by reference.

Todd W. Murray, Hemmo Tuovinen, and Sridhar Krishnaswamy, have written an article entitled "Adaptive Optical Array Receivers for Detection of Surface Acoustic Waves." See *Applied Optics*, vol. 39, No. 19, pp 3276–3284 (2000). This article describes a method for collecting a number of discrete laser beams and coherently combining them in a nonlinear photorefractive crystal with a coherent reference so that a single beam (the coherent reference) emerges with all phase information of the input beams imprinted onto this output coherent reference beam. The goal of this device is to pre-process a finite number of input beams so that the ensemble can detect surface waves on an object of interest. The disclosed device enables one to coherently combine a number of probe beams, each of which interrogates a given object at strategically located and predetermined locations on its surface, so that any surface wave can be sampled. The specific goal of the crystal is to provide a single output beam, encoded with the phase information from all of the initial probe beams. In order to subsequently determine the nature of any surface wave, the encoded beam then needs to impinge upon a heterodyne or homodyne optical receiver, equipped with a square law detector and yet another coherent reference beam to reveal the desired phase information. Since most photorefractive crystals are slowly responding, the system can only operate over a limited bandwidth of mechanically induced background noise (whose phase noise is undesirable). Moreover, each probe beam, after reflection from the surface of interest, must each be directed separately onto the crystal. Therefore, that which is needed is a novel image relay system that enables one to employ a single probe beam that illuminates the surface in question with a unique optical pattern (selected to probe a given acoustic mode, be it a surface wave, an internal compression wave, etc.). Furthermore, the optical pattern that strikes the surface should preferably be in the form of a continuous optical pattern, as opposed to a countable number of spots, as in the prior art.

In U.S. Pat. No. 6,008,887, by Klein et al., a single beam laser apparatus for measuring surface velocity at acoustic frequencies and surface displacement at ultrasonic frequencies is disclosed. This apparatus includes a source laser and optics for directing a single laser beam at normal incidence to a surface. A photo EMF detector and optics are provided for directing a surface reflected laser beam at the photo EMF detector in order to provide outputs that are directly proportional to all three orthogonal components of surface velocity or displacement. This patent involves a photo-emf sensor with a crossed electrode configuration, so that motion of an optical pattern can be sensed if the pattern moves arbitrarily in the plane, in both orthogonal directions. This enables one to detect in-plane motion of a non-specular (diffusely scattering) object, in which case, an optical probe beam emerges as a highly speckled beam. This beam, when impinging onto the disclosed photo-emf detector, will result in a dynamic, laterally shifting speckle pattern, in response to a corresponding lateral motion of the object. There is no suggestion in this patent about phased-array detection of a specific acoustic mode of a given object. Indeed, this disclosure teaches that a single laser probe beam interrogates a specific location on the surface of the object.

Therefore, there exists a need in the art for an ultrasonic non-contacting inspection system that incorporates the use of a single element photo-EMF sensor to perform phased array sensing of ultrasound signals to reduce the complexity and cost of prior art systems.

SUMMARY

The presently disclosed technology may be utilized as an ultrasonic single element non-contacting inspection system which preferably includes a laser to generate ultrasound, a laser to probe the sample for the ultrasound, and a receiver.

A single element photo-EMF detector element is preferably utilized to emulate phased array sensing of ultrasound signals using a single sensor. Preferably, due to the robustness of the disclosed detector system, the sensing of an arbitrary phased array pattern can occur without the need for a discrete set of sensors or for a specific electrode configuration. The embodiments of the presently disclosed technology can be utilized to provide the ability to realize high spatial resolution acoustic imagery with relatively low laser fluences, as well as the ability to reduce incoherent noise clutter and spurious signals from high scattering off-axis acoustic sources. This incoherent noise reduction is due to the fact that a phased-array detection scheme is proposed. Incoherent noise would result in a randomly phased response from each spatially resolvable "pixel" on the surface. Hence, the resultant coherent summation of this ensemble of random-phased signals will tend to zero. That is, the phasor summation will tend to zero, since, for a given phase detected in the array at one location, there will, on the average, be another element of the array that detects a signal with an opposite phase at another location. On the other hand, the desired signal to be sensed will possess the same phase throughout the ensemble, so that its coherent summation will be maximal as opposed to zero.

The disclosed ultrasonic inspection apparatus and method permits the inspection of delicate materials, which require a system to operate in the thermo-elastic mode. The inspection of delicate materials also requires sensitive diagnostic equipment owing to the low laser energies absorbed by the delicate material along with potential spurious modes. The disclosed system provides a high resolution, high sensitivity system preferably utilizing a single element detector.

One feature of the disclosed technology is that a relatively low-power laser source may be used to excite the sample under evaluation. By utilizing reduced excitation-laser power levels, one can avoid irreversible surface damage by operating in the thermoelastic mode of excitation. However, this comes with a cost of generating weak acoustic beams in a thermoelastic mode. This follows since this mode of excitation does not usually provide strong surface vibrations (to be read out by a probe laser), given that the excitation laser source is weak and, moreover, that the resulting acoustic waves are spread over a wide angular cone, providing low-intensity acoustic modes that radiate over a wide area. This leads to the production of relatively small read-out surface vibrations, which are probed by the read-out laser beam with a typical beam width of one or two mm. The result is that the phase modulation encoded onto the read-out laser reflecting from the vibrating surface of the workpiece is very small and the detected S/N ratio is low, possibly leading to the need for long dwell times of the probe beam at a given surface location. One method to enhance the S/N is through the use of phased-array sensing.

We have previously disclosed in our U.S. Pat. No. 6,075,603 how an annular ring of detectors, serviced by an annular ring read-out laser, can sample a much larger read-out surface, with the extended size of the sound wave sampling system generating high precision angular resolution of a buried scatter source. Further, the associated S/N can be substantially improved by this operation via a judicious choice of the locations of the excitation laser spot that impinges onto the sample and the location of the annular laser optical pattern on the sample relative to the excitation laser spot. In most cases, the system is optimized when the excitation laser spot is located at the center of the probe laser ring pattern. The reflected or scattered probe laser ring pattern is them imaged or relayed to an annular array of sensors (in the prior art). Since each detector element in the array provides an independent sensor for the desired signal as well as for the undesirable noise background, the S/N for this geometry is enhanced by electronically summing up the output from the array of detectors. This enhancement follows since, by symmetry, the summed output of the desired signal component combines coherently, while the detector noise components add incoherently. The present invention retains these desirable features with the simplification that all of the detectors are merged into a single-element, distributed photo-EMF detector.

There are two basic embodiments that can be realized using this technology: spatial averaging of internal features of a workpiece in one case, and high-resolution imaging of internal features of a workpiece in another case.

In the first case, we note that not all applications are concerned with high-resolution defect imaging of hidden features. That is, cases exist where it is of interest to measure globally averaged elastic properties of a material (such as density, hardness), as well as temperature and sample thickness. Such globally averaged workpiece properties can be remotely measured using the system consisting of a single-spot excitation laser, and an optical ring pattern for the probe laser, with the latter light imaged onto a single-element distributed sensor for equivalent phased-array detection. Since the thermoelastic excitation from a single laser spot results in a conical acoustic emission pattern in the material (of broad angular range), the resultant acoustic vibrations sensed by the annular ring pattern of the probe laser essentially provide some spatial averaging of the acoustic propagation effects of the material. This is desirable in the case of bulk material measurements, such as hardness, thickness, temperature, etc. Since random material defects and internal inhomogeneities will be effectively averaged out (i.e., offset) due to the broad range of acoustic paths sampled throughout the workpiece, that would otherwise result in systematic errors in such bulk material measurements.

The second case pertains to applications where detailed, high-resolution internal imaging within a workpiece is desired (as opposed to spatial averaging, as in the first case above). Examples here include the mapping and sensing of internal defects, voids, inclusions, microcracks, and delaminations in various materials, such as metals, coatings, composites, etc. Thus, for systems intended to find and localize such buried damage sites, the wide angular sound pattern (in the first case above) impedes high-spatial resolution of the specific location of the buried scatter source, or defect. We herein describe how this simplified (equivalent phased array) receiver can be combined with an annular ring laser excitation source, which further improves flaw location accuracy and detector S/N. This enhanced spatial resolution results from the fact that a ring pattern for the excitation laser induced an internal acoustic radiation pattern consisting of overlapping conical emission patterns, which result in spatial regions of enhanced acoustic excitation at localized regions in the workpiece where the overlapping occurs. Moreover, the symmetry of the laser probe ring pattern, by reciprocity, also samples localized regions within the workpiece with enhanced S/N owing to the coherent summation from those regions. Thus, the net system sensitivity is, effectively, the mathematical product of the pair of spatial patterns of the excitation and detection functions. This results in a very localized coherent summation, whose signal can be mapped by merely changing the radius and width of the pair of optical ring patterns (either separately or in combination).

Embodiments described herein can provide an improvement over systems based on arrays of detectors, since a single detector is lower in cost and complexity than an array of detectors. One skilled in the art will appreciate that additional elements can be added to provide electronic beam steering or focusing; however, embodiments of the present invention realize a simple effective phased array type of sensor without the need for a custom detector design.

Embodiments described herein can emulate phased array detection without the need for an array of discrete sensors. Embodiments of the present invention allows for a reduction in system complexity, reducing an array of sensors of approximately 100 down to a single detector element. Further, the electrode pattern of this detector can be made very simply: just a set of parallel electrodes or a pair of concentric electrodes, depending on the geometry. Thus, embodiments of the present invention provide a simple, low cost, highly functional detector.

In one aspect the presently disclosed technology provides an ultrasonic inspection system comprising: a laser generator for impinging a workpiece with light for generating a thermo-elastic acoustic reaction in a workpiece; a probe laser for impinging the workpiece with an annularly-shaped probe light for interaction with the acoustic signal in the workpiece resulting in a modulated return beam; a reference signal generator; and a photodetector having a sensitive region for detecting an annularly-shaped fringe pattern generated by an interaction of the reference signal and with the modulated return beam at said sensitive region.

In another aspect the present invention provides a method for inspecting a workpiece comprising: generating a thermo-elastic acoustic signal in said workpiece; optically sampling said thermo-elastic acoustic signal using an annularly-shaped probe beam; generating a reference signal; and detecting, utilizing a single detector, a fringe pattern generated by an interaction between said reference signal and said optically sampled thermo-elastic acoustic signal.

BRIEF DESCRIPTION OF THE DRAWINGS

The features and advantages of the presently disclosed technology will become better understood with regard to the following description, appended claims, and accompanying drawings, wherein:

FIG. 3 depicts another embodiment of an ultrasound inspection system in accordance with the present invention;

FIG. 3a depicts one possible modification to the embodiment of FIG. 3;

DETAILED DESCRIPTION

Figure 1:
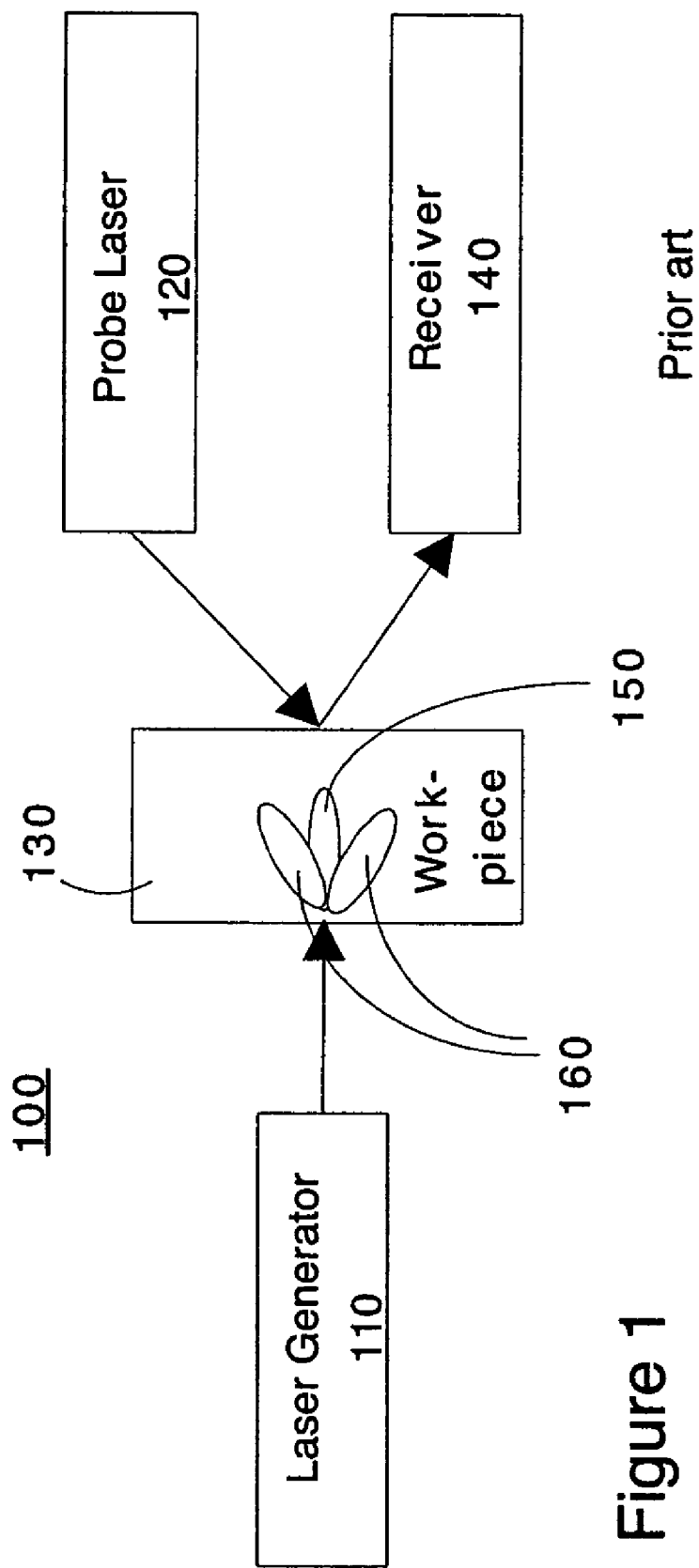
FIG. 1 depicts a cross-sectional, simplified view of a conventional prior art laser-based ultrasonic detection system architecture.

The presently disclosed technology will now be described more fully hereinafter with reference to the accompanying drawings, in which preferred embodiments are described. The presently disclosed technology may be embodied in many different forms and should not be construed as limited to the embodiments set forth herein. Further, the dimensions of certain elements shown in the accompanying drawings may be exaggerated to more clearly show details. The present invention should not be construed as being limited to the dimensional relations shown in the drawings.

FIG. 1 depicts a cross-sectional, simplified view of the architecture of a conventional prior art ultrasonic inspection system. The ultrasonic inspection system 100 of FIG. 1 comprises a laser generator 110 for generating an ultrasound signal directed toward a workpiece 130, a probe laser 120 for sampling the ultrasound from the workpiece 130 and a receiver 140. The beam from the laser generator 110 may be focused onto a single spot on the workpiece 130 or a general pattern (e.g. an annular ring) to generate the ultrasound. When the beam from the probe laser 120 is focused onto a single spot on the workpiece 130, the result is equivalent to a single transducer placed on the part (without loading). When the beam from the probe laser 120 is configured to generate a general spatial pattern, the ultrasound is sampled at a plurality of points, which can be configured into a resultant phased array of equivalent detectors.

There are two modes of ultrasonic generation that can be realized by the laser generator 110. The two modes are depicted in the cross-sectional view of the workpiece 130 of FIG. 1. In one mode, the laser fluence is sufficiently high so that a mild degree of surface ablation is realized on the part. Surface ablation results in the removal of a small amount of surface material from the workpiece 130. In this ablative mode, a compressional acoustic wave 150 is generated in the workpiece 130. This wave 150 propagates essentially in a direction normal to the surface of the workpiece 130.

Another laser acoustic mode of generation is called the thermo-elastic mode. In the thermo-elastic mode, the surface of the workpiece 130 is not damaged, yet an ultrasonic wave is generated. In cases where the workpiece has a low damage threshold, or it is undesirable to have even cosmetic surface damage on the workpiece, ultrasonic generation in the thermo-elastic mode is desirable. In these cases, the fluence of the laser generator 110 is constrained to be below the ablation threshold, and thus only the thermo-elastic mode is generated. The thermo-elastic radiation pattern is conical, with the thermo-elastic acoustic wave 160 propagating at an angle, centered at about 60°, with respect to the normal of the surface of the workpiece 130 as shown in FIG. 1.

One method of efficiently detecting the thermo-elastic acoustic wave 160, involves the laser generator 110 producing an annular ring of light onto the workpiece 130. The resultant beam is directed from the workpiece 130 toward the receiver 140, wherein the receiver 140 preferably comprises an annular array of detector elements. The output of each of the detector elements can then be combined electronically to enable a high resolution image of internal scattering sites, excited by the acoustic radiation pattern. In addition, by adaptively processing the detected information, the inspection system may provide electronic scanning as well as focusing of the detected information.

It has been previously shown that an array of photo-EMF detectors can be arranged in an annular ring to service a non-contacting laser-acoustic imaging system, providing excellent scatter-site (lateral) location accuracy, of the order of 1 mm (at a sound frequency of 10 MHz). However, the point spread function (PSF) of this imaging system has rather high side-lobe levels that can generate false scatter defect information (the PSF is a mathematical function that provides a measure of the spatial resolution of an imaging system, and, high-side-lobe levels are indicative of degradation in the imaging resolution of the system). For example, the maximum side-lobe level (for objects buried at about the ring diameter) is about 40% of the peak value. We show herein how this imaging receiver can be supplemented with a narrow-beam, co-axial, acoustic transmitter being employed to reduce the ensemble system point spread (PSF) side-lobe levels. Further, this combination reduces the PSF main lobe width, appreciably improving the ensemble system resolution. Still further, this transmitter can preferably operate with a thermo-elastic excitation laser, operating with low-peak values of laser irradiance and avoiding the surface damage associated with ablative excitation. Still further, the magnitude of the sonic scatter-site illuminator beam, formed on the axis of the system, is greatly enhanced (for a given excitation laser power density) by the use of an annular ring probe-laser illuminator pattern, which in turn greatly improves the detector S/N level.

Although a basic point-source (single laser spot) thermoelastic excitation sound wave pattern is very broad (approximately 30 degrees) and would contribute very little to system resolution, the use of an annular-ring laser excitation pattern results in a continuum of overlapping thermoelastic beams producing relatively strong on-axis peak via constructive interference. The off-axis acoustic excitation beams overlap to produce substantially destructive interference, with the acoustic beam intensity pattern falling off rapidly upon departure from the axis of the excitation source. This transmitter PSF pattern shape is largely independent of depth in the workpiece and is closely similar to and complements the receiver PSF, with the system resolution determined by the composite PSF, being approximately the square of either pattern. Thus, the strongest system side-lobe is reduced from about 40% to 16%, with still greater improvements in the weaker side lobes. Since the PSF can be predicted once the scatter-site depth is known (via receive signal time-of-arrival), further side-lobe suppression is possible by post detection processing using computer deconvolution.

It should be noted that no focusing of the on-axis illuminator sound beam is required, which permits rapid mechanical scanning of the laser read out and the sonic generator laser beams, since one need not pause for focus adjustments. The use of single-sided excitation and detection operation (as illustrated) is preferred in this case.

Figure 2:
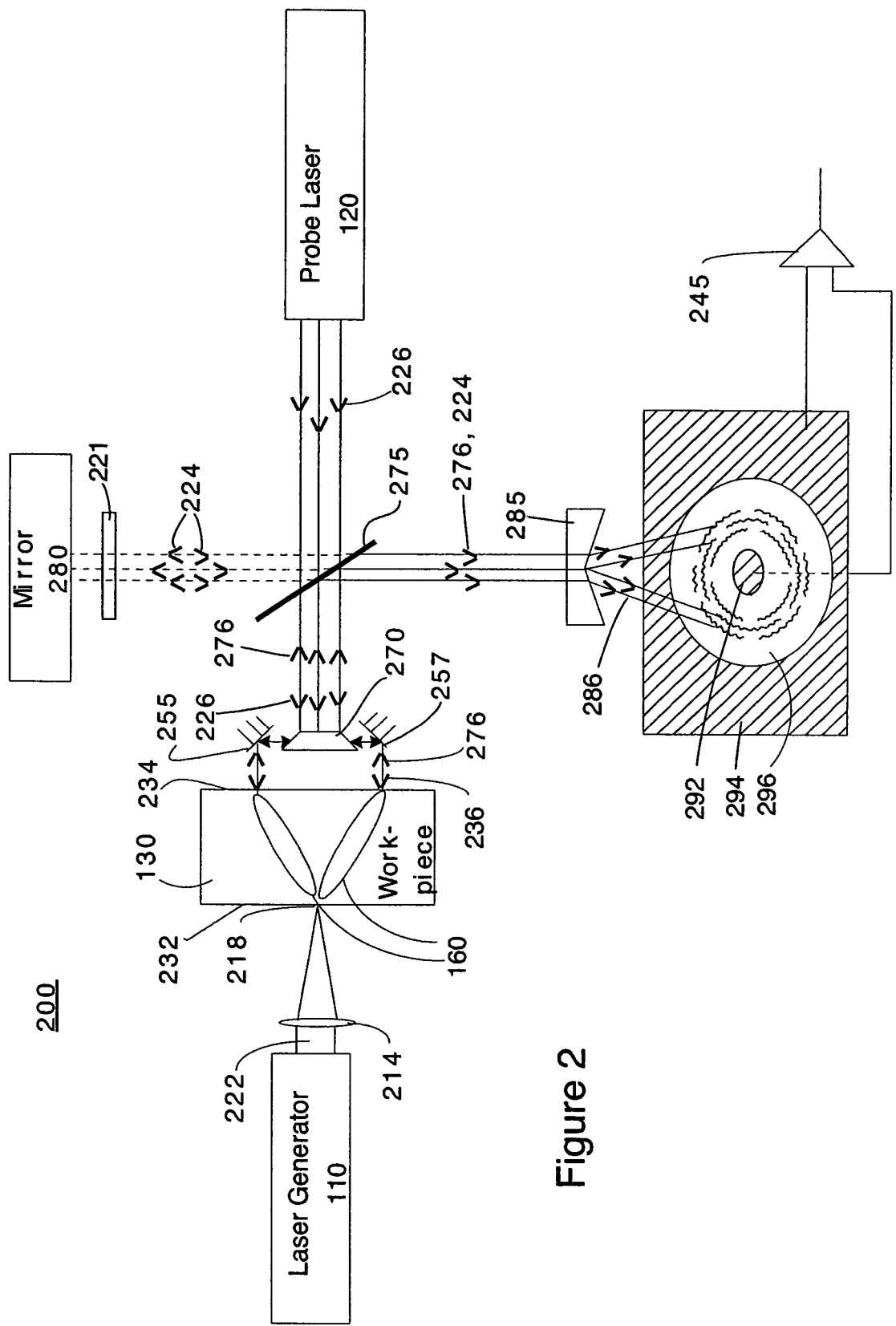
FIG. 2 depicts an embodiment of an ultrasound inspection system in accordance with the present invention.

FIG. 2 depicts an embodiment of an ultrasound inspection system 200 in accordance with the presently disclosed technology. This embodiment 200 enables efficient detection of the thermo-elastic mode. As illustrated in FIG. 2, the inspection system 200 generally comprises a laser generator 110, a probe laser 120, and a single detector 290.

The laser generator 110 preferably generates a pulsed beam 212 that is focused by a lens 214 to form a single spot 218, on the surface 232 of the workpiece 130, i.e., preferably at relatively low power intensities. The single spot pattern 218 generates thermo-elastic acoustic waves 160.

It is well known in the art, that at relatively low laser intensities, the acoustic excitation mode is primarily thermo-elastic in nature. In this regime, the material is not modified permanently, and the process is reversible. At relatively higher intensities, both the thermo-elastic as well as an ablation mode can be induced by the laser as it impinges onto the sample. Since the surface is ablated (mildly at lower intensities and in a greater manner at yet higher intensities), the process is not reversible, since the surface may be permanently modified, superficially modified, or permanently damaged. The threshold intensity that defines the ablation excitation mode is highly material dependent, as well as laser pulse-width and laser wavelength dependent, and, can vary over orders of magnitude. For example, for a Q-switched laser pulse (typically 10 nanoseconds in duration) incident onto a metallic surface, the ablation mode can occur for a mildly focused laser spot (beam size of a millimeter or less) whose peak intensity exceeds 10 megawatts per square centimeter (since this is the peak intensity, the average laser power can be very low, say 10 watts, depending on the pulse repetition rate), corresponding to laser energies in the 10 milijoule to 100 milijoule range per pulse at about a 1 micron wavelength. For paper, composite materials, and delicate coatings, the ablation threshold can be orders of magnitude smaller than noted above.

For the purposes of this disclosure, relatively low power intensities for an laser refer to those intensities where the acoustic excitation mode is primarily thermo-elastic in nature rather than ablative.

The acoustic pattern 160 within the workpiece 130 is a conical acoustic wave that propagates into workpiece 130. This particular acoustic mode is typical of a low-intensity excitation laser that is focused at a single point on the surface 218 of the workpiece 130. Generally speaking, a laser generator 110 with multiple spots that illuminates the workpiece 130 can alternatively be used, in which case, a phased-array excitation acoustic mode can be realized via thermo-elastic excitation, ablation excitation, or a combination of these two mechanisms. The notion of using a laser (or multiple lasers) to generate a phased-array excitation mode is well known in the prior art (see the discussion in the book by Scruby and Drain mentioned above).

The presently disclosed technology deals with, among other things, novel methods for equivalent phased-array detection, and the disclosed systems can accommodate single-point lasers as well as multi-point laser excitation (as well as other general forms of acoustic excitation, be it conventional transducers, etc. as well as internally generated acoustic excitation, the latter sometimes referred to as "acoustic emission").

The thermo-elastic acoustic pattern 160 shown in FIG. 2 is one example of many classes of acoustic modes that can be induced by a laser exciter (other modes include compression waves, surface waves, Lamb waves, etc.), which are also well known in the art. In the context of the presently disclosed technology, different detection patterns may be suitable to enable phased-array detection of other excitation modes, but, in general, the presently disclosed technology preferably utilizes a single element photo-emf sensor to emulate phased-array detection with a single device by virtue of the symmetry of the sensor and the laser probe beam as well as the symmetry of the incident optical fringe pattern and its motion, as induced by the surface vibrations of the workpiece.

For operation in the thermo-elastic regime, the power density of the pulsed beam 212 at the surface 232 should preferably be kept below approximately 10 MW/cm$^2$. At such power densities, the thermo-elastic acoustic waves 160 are generated by the thermo-elastic stresses and strains that are induced by localized heating of the material. The main advantage of operating in the thermo-elastic regime is that the workpiece 130 is not damaged by the pulsed beam 212. Of course, if damage of the workpiece 130 is of no concern or if the workpiece 130 is robust, then a higher power laser may certainly be used, which can generate thermo-elastic excitation, ablation induced excitation or a combination of the two.

The thermo-elastic acoustic waves 160 propagate through the workpiece 130 and vibrate its outer surface 234. The thermo-elastic acoustic waves 160 arrive substantially in phase over an annular ring locus at the outer surface 234.

The vibrating surface is then optically probed. This is accomplished by using probe laser 120. The probe laser 120 is preferably a continuous-wave (CW) or long-pulse laser. The probe laser 120 generates a probe beam 226 that is subsequently split into a reference beam 224 and a readout beam 227 preferably by a polarizing beam splitter 275. Other components can be used to split the beam 222, including a conventional (non-polarizing splitter) or a Bragg cell. A conventional beam splitter can be used, but as long as the workpiece 130 does not depolarize the incident light, the use of a polarizing beam splitter 275, in conjunction with a quarter wave plate 221, will enable more optimal use of the light (e.g. with less optical loss). A Bragg cell would require postprocessing, so, a passive, polarizing beam splitter 275, as shown in the FIG. 2, is preferred. The reference beam 224 is directed toward a mirror 280. The readout beam 226 is used to readout the acoustically induced displacement of the outer surface 234 of the workpiece 130.

The intensity of the readout beam 226 is preferably much higher than the intensity of the reference beam 224. A high intensity readout beam 226 helps to overcome the low optical reflectively and/or high optical scattering that are typically exhibited in workpieces 130.

After the readout beam 226 passes through the polarizing beam splitter 275, the readout beam 226 is focused by an axicon 270 and mirrors 255, 257 to form a spatial light pattern 236, preferably a ring shaped or annular pattern, on the vibrating surface 234 over the locus 236.

A portion of the readout beam 236 is reflected and phase modulated by the vibrating surface 234. The modulated readout beam 276 is then collected by the mirrors 255, 257 and axicon 270 and directed back through the beam splitter 275. The beam splitter 275 reflects the modulated readout beam 276 toward a modified axicon 285.

The modified axicon 285 relays the modulated readout beam 236 in the form of a conical signal beam 286 and, at the same time, generates a conical reference beam 298 from the incident reference beam 224. The two conical beams contact the surface of detector 290 at slightly different angles to thereby form interference fringes necessary for the detector 290 to sense the phase shift of the modulated readout beam 236 (as converted to its conical signal beam 286 format) relative to the reference beam 224 (as converted to its conical reference beam 298 format). In the present embodiment, a set of concentric interference fringes are generated (a.k.a. Newton's rings) on the detector 290. For additional information regarding a modified axicon 285, see U.S. Pat. No. 6,075,603 to O'Meara and Pepper, mentioned above.

Mirror 280 is preferably a planar mirror. However, in some embodiments mirror 280 can be a curved (spherical) mirror, so that, in conjunction with the modified axicon (as described in U.S. Pat. No. 6,075,603), the desired annular interference pattern forms on the surface of the photo-emf detector 290. The distance the light travels from the splitter 275 to the workpiece 130 is preferably the same as the distance it travels from the splitter 275 to mirror 280 and, if there is any difference in the lengths of these two optical paths, the difference should be less than the coherence length of the probe laser 120 in order to form a suitable fringe pattern at detector 290.

The detector 290 is preferably a single photoinduced EMF detector, e.g. a GaAs detector. The geometry of the detector 290 preferably comprises a round central electrode 292 with a concentric circular outer electrode 294. A small annular region on the detector plane provides an active area 296 of the detector. The modulated readout beam 276, which is preferably a ring pattern of light, is directed onto the active area 296 bounded by the two concentric electrodes 292, 294. As discussed above, the conical reference beam 298 (derived from reference beam 224) spatially overlaps the modulated conical readout beam 286 (derived from beam 236) on the active area 296 creating a set of concentric interference fringes (shown by the dashed lines) in the active area 296. When the workpiece 130 experiences an acoustic excitation, these rings will "breathe" in and out (i.e., they will compress and expand in radius, concomitant with the vibration amplitude and frequency of the workpiece 130 under inspection). The electronics include a transimpedance amplifier 245. Also, owing to the properties of the photo-emf sensor 290, no phase-locked loops or tracking circuits are required to track noise and mechanical vibrations typical in a manufacturing environment, nor are servo loops needed to ensure phase quadrature between the pair of interfering beams (reference and object) on the sensor's surface. Instead, the photo-emf detector 290, in effect, performs all of these necessary operations (tracking of mechanical noise, tracking, quadrature locking, speckle compensation, etc.) optically by its nonlinear optical response.

FIG. 3 depicts another embodiment of the presently disclosed technology, which embodiment may be used for ultrasonic inspection. The common character references represent similar and preferably equivalent elements as earlier set forth and described in connection with FIGS. 1 and 2. The detector 390 in this embodiment comprises a large area detector element with parallel electrodes 392, 394. The area of the detector 390 between the parallel electrodes 392, 394 is the active area 396 of the detector 390. The active area 196 is preferably of a square or rectangular configuration. The ring pattern created by the modulated readout beam 276 is the same as described with reference to FIG. 2. However, the reference beam 324 in this embodiment is no longer a conically offset version of the probe beam 226 as described in reference to FIG. 2. Instead, in the embodiment shown in FIG. 3, a beam splitter 375 is placed between the probe laser 120 and the first beam splitter 275, the beam splitter 375 directing a portion of the probe beam 226 toward detector 390 via an optical path which, in this embodiment, includes a mirror 355. This portion of the probe beam 226 creates a flooding reference beam 324. Mirror 355 is used in this embodiment to direct the flooding reference beam 324 onto the detector 390. The flooding reference beam 324 is designed to cover preferably the entire active area 396 with a constant angular offset. Thus, a set of near parallel fringes are generated, with modulated readout beam 236 forming the boundary where the interference occurs. The result is an annular ring pattern 398 formed on the detector 390 due to the interference between the modulated readout beam 276 and the flooding reference beam 324.

It should be noted that the interfering beams need not both illuminate the entire surface of the photo-emf sensor 390. This is in contrast to a conventional coherent detector, which requires spatial overlap of both the reference and signal beams over its entire surface for optimal performance. In this embodiment, the photo-emf sensor 390 will respond to the dynamic changes in the desired interference pattern on its surface (in the present case, formed by the localized overlap of the annular pattern from the axicon 270 and the plane wave from the reference beam 324) even though both beams do not overlap across the entire sensitive surface 398. An important advantage of this embodiment is the fact that the photo-emf sensor 390 will function as long as at least one of the aforementioned beams covers the entire surface 396; that is, the second beam need not cover the entire surface. In general, there will be localized regions on the surface 398 where both beams overlap, and, hence, localized "patches" of interference patterns. This greatly simplifies the system architecture, in that only one of the beams need to cover the active area entirely. This is most easily accomplished by having the reference beam 324 "flood" the sensor's active area 396, since, in general, the beam 276 scattered from the workpiece 130 may not emerge as a uniform beam (for example, there may be holes in the workpiece 130, nonreflective regions, angled regions, etc.). In spite of this, this embodiment will still function, since the phased array or, equivalently, the co-phased nature of the presently disclosed technology will enable coherent summation of all the resultant interference "patches" and minimize incoherent contributions, as discussed earlier.

The embodiment shown in FIG. 3 has the benefit of less complexity because the flooding reference beam 355 need not match the pattern of the modulated readout beam 276. Further, in the embodiment shown in FIG. 3, the area 399 of the detector 390 inside and outside the annular ring fringes 398 is made conductive by the finite photoconductivity of the detector active area 396 in the presence of the flood reference beam 355. Thus, the class of detector 390 can be very general due to the global photoconductive region created by the flooding reference beam 324 surrounding the region of interference 398. Region 298 is an optical interference pattern whose fringe pattern moves ("jitters") in the directions of electrodes 392, 294 in response to information gained from the workpiece 130.

In the embodiments shown in FIGS. 2 and 3, a finite photo-EMF current will be realized, as long as the desired acoustic signal is in phase (that is, as long as the surface displacements sensed by the optical probe beam occur within a fraction of an acoustic period wherein an acoustic period is generally on the order of a microsecond). For spurious signals, the photo-EMF currents will not add in phase across the detector 290, 390 surface; therefore, a very small current will result. Thus, an equivalent phased array mode of detection is realized with only a single detector 290, 390. One skilled in the art will appreciate that knowledge of the surface metrology of the workpiece 130 can be used to deconvolve temporal dispersion of the sensed signal.

Instead of focussing the laser beam 22 onto a point 218 on a surface of the workpiece 130, the beam laser beam 222 can be set up to probe the workpiece 160 and to scatter from a small (sub-acoustic wavelength) defect 218*a* (see FIG. 3*a*). The defect can be a surface defect or, as shown, an internal defect. The acoustic wave 201 generated by the probe beam 222 will be scattered, into a different set of directions 202, as if it were generated at a point source.

A further benefit of these embodiments is that the probe beam 226, as it probes the surface 234 of the workpiece 130, is formed as an annular ring of light by axicon 270, and is preferably approximately matched in radius to the expected radius of the acoustic pattern 160 in the workpiece 130 that is expected from the thermo-elastic mode to be sensed. Hence, a matched filter is effectively realized that is optimized to the desired acoustic mode in the workpiece 130.

Figure 4:
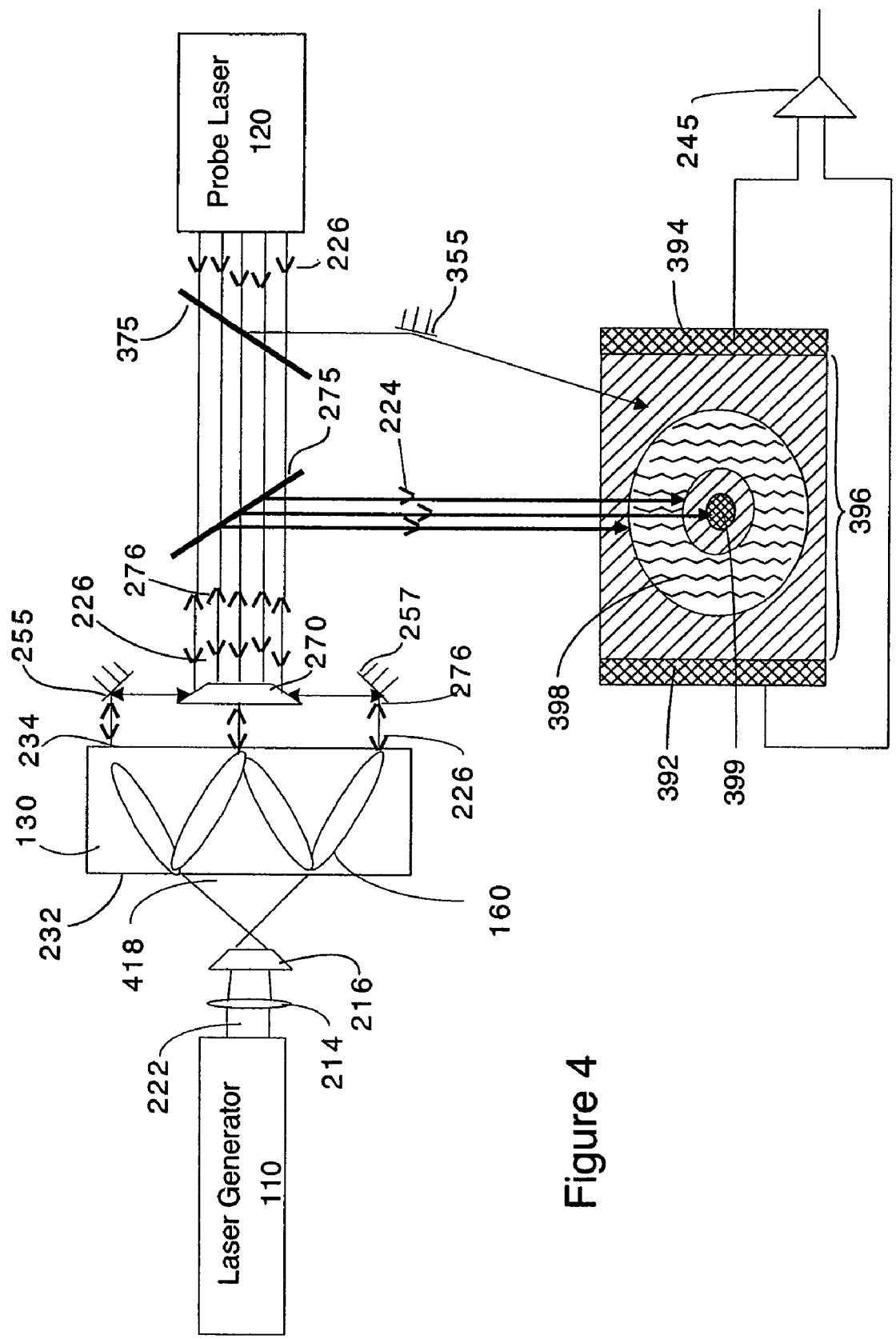
FIG. 4 depicts another embodiment of an ultrasonic inspection system, this embodiment utilizing a matched ring transmitter optical pattern with a single detector providing both a point receiver and an annular receiver.
Figure 5:
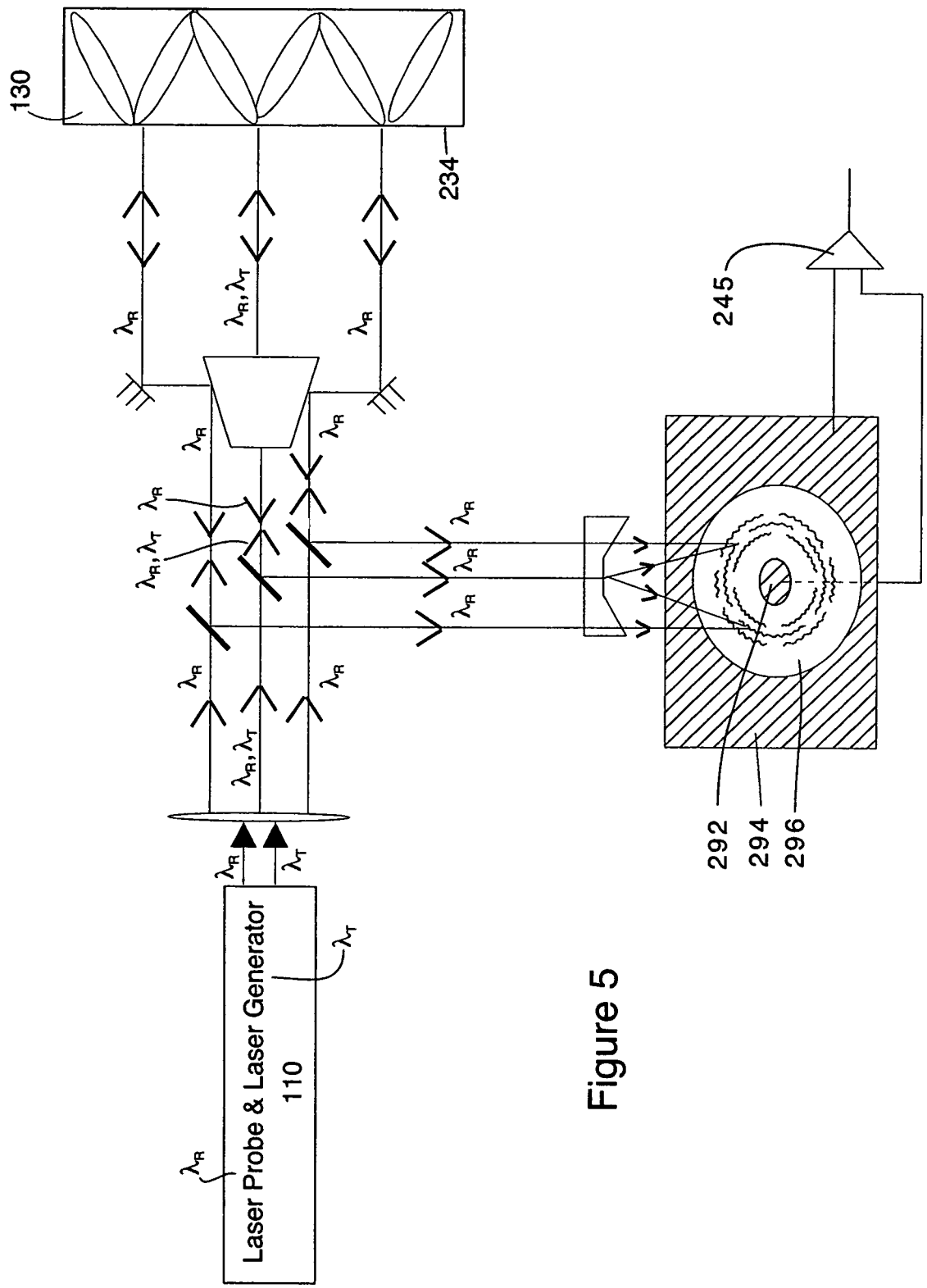
FIG. 5 depicts yet another embodiment of an ultrasonic inspection system, this embodiment being able to generate and sense an acoustic mode from the same side of the sample.

FIGS. 4 and 5 depict other embodiments of ultrasonic inspection systems. In FIG. 4, an ultrasonic inspection system 400 is depicted that involves a matched ring transmitter optical pattern with a single detector 390 providing both a point receiver 399 and an annular receiver 398.

The laser generator 110 preferably generates a conical acoustic radiation pattern 418 on the workpiece 130 using a lens 214 and an axicon 216. So elements 110, 214 and 216 provide an annular ring transmitter which generates a conical acoustic radiation pattern 418 which strikes the workpiece 130 and after striking workpiece 130, it is transformed by axicon 270 into (i) an annular pattern which strikes annular receiver 398 and (ii) into a focused acoustic spot for receiver 399 along its axis. The axicon 270 generates an annular ring pattern in region 398 of the active area 396 of the photo-emf sensor 390, which is a result of the probe light 226 that reflects from the outer portion of the axicon 270 and strikes the workpiece 130. In addition, the probe light 226c that travels down the optical axis of the system goes through a central region of the axicon 270 (and is not reflected off-axis) and simply strikes the surface 234 as if no optical element were present. That is, it hits the surface 234 "head on". This central beam 226c therefore samples vibrations along the optical axis of the system. By symmetry, the phase of the resulting central modulated beam 276c, induced by the acoustic wave in the workpiece 130, will be in sync with that of annular region 276. Hence, by employing a sensor 290 with the electrode pattern shown in FIG. 4, the two different output signals can be detected by a single sensor: the phase-coherent output due to the annular region as well as the vibrations of the object along the optic axis of the system.

The probe beam 226 samples the workpiece at the locations where the thermo-elastic wave 160 reaches the surface 234 of the workpiece 130. The modulated readout beam 276 and the flooded reference beam 324 form an annular beam with parallel fringes which is imaged on an annular ring 398 portion of the detector 390 and a central spot, also with parallel fringes, which is imaged on the central point receiver 399 of the detector 390.

The off-axis reference beam 355 "floods" the detector 396. Two different interference regions, an annular region 398 and a spot-like region 399 will result with the fringes in both regions 398, 399 moving towards and away from electrodes 392, 394 in a synchronized fashion (i.e. in phase with the presence of the excitation pattern 160).

Every point on the transmitter light ring 418 acts as a point source of acoustic waves 160 through thermo-elastic effects. Therefore, the transmitter light ring 418 actually generates an array of acoustic waves that arrive in phase at points in the workpiece 130 that are centered with respect to the transmitter light ring 418. At these points, the acoustic waves 160 coherently add, resulting in an acoustic beam having a finite diameter that is smaller than would be produced by a typical (1 mm to 2 mm) single laser illumination spot. The diameter of the acoustic beam at any given depth is a function of the transmitter light ring 418, the wavelength of the acoustic beam and the distance from the transmitter light ring 418.

Therefore, the diameter of the transmitter light ring 418 can be adjusted so that the coherent addition of the acoustic waves 160 at a specified position in the workpiece 130 result in a narrow acoustic beam at the specified position.

In FIG. 5, a system is shown that can generate and sense an acoustic mode from a common side 234 of the workpiece 130 (same surface pitch-and-catch). Thus in FIG. 5, both the laser excitation beam as well as the laser probe (or, interrogation) beam impinge upon the same side of the object under test. This architecture is useful in situations where access to a given part is limited to a single surface, such as surfaces on the exterior of aircraft, engines, certain microelectronic circuit boards, pipes, etc.

In this embodiment two lasers are employed (at least conceptually) in the box labeled 110: one for excitation and one for interrogation. Note, however, two separate lasers need not be used; instead, a single laser, perhaps with polarization decoupling or WDM decoupling can be employed. In this figure, the central beam 226c emanating from the laser 110 (of the three beamlets shown) preferably consists of beams from both lasers which are overlapping, whereas the outer beamlets 226 consist of laser light from only the receiver laser (the interrogator). Thus, the central beam 226c serves two functions (excitation and interrogation), whereas the other two depicted beams 226 from laser 110 form an annular ring pattern on the workpiece 130 (in a similar fashion as done in the previous embodiments).

By use of a diachronic dielectric coating the front face of axicon 270, the axicon reflects light from the receiver laser, while passing light from the transmitter laser, which strikes the workpiece 130 and generates the photo-acoustic or ultrasonic acoustic waves 160 in the workpiece 130. Some of this acoustic energy traverses the workpiece 130, reflects from its back surface and strikes its front surface where the outer annular probe beam 226 is located. The light scattered from the outer ring region is collected by the axicon 270 and is relayed to the photo-emf sensor 290. The probe beam that reflects from the front surface of the axicon 270 acts as the reference beam which, after passing through the second optical element (the previously discussed modified axicon 285), forms a set of annular interference rings on the sensor 290 in its active region 296 as in the previous embodiments.

In FIG. 5, with respect to $\lambda_R$ and $\lambda_T$, the subscripts "R" and "T" indicate the laser receiver (interrogator) and laser transmitter (exciter) wavelengths, respectively. As discussed above, orthogonal polarizations can also be used to decouple the two laser beams.

A parallel electrode detector can be used as a same side inspection system. The desired acoustic mode to be detected must have a symmetry consistent with the corresponding symmetry of the electrode pattern on the detector to yield the desired (or, preferred) phased array sensing. Hence, in principle, a parallel electrode sensor can also be employed, with the proviso that the desired acoustic mode to be sensed has a similar symmetry.

The preferred materials for the detector 290, 390 are: semiconductors (GaAs, CdS, multiple quantum wells), oxides (BSO), etc. These are well known in the art and therefore are not discussed in further detail here.

The specific laser type(s) used will be a function of the material of the workpiece 130 to be inspected (optical absorption coefficient, optical damage threshold, pulsed versus continuous, etc.). The choice of laser parameters will also dictate the optical components required, which are well known by those skilled in the art. Similarly, the spacing between the laser system and the workpiece 130 under test will be a function of the optical scattering properties of the materials to be evaluated and the collection efficiency of the optical system (aperture size, f/#, etc.), cost, weight, etc.

In order to obtain good spatial resolution with annual sources and receivers, it is desired that the sound wave frequency content be restricted to high frequencies, preferably starting at about 5 MHz. A three-to-one, or four-to-one frequency range is typically employed (for example 5 to 15 MHz or 5 to 20 MHz. This provides a good compromise between temporal and spatial resolution.

For some applications, there are additional advantages to high frequency sound-wave sources. These include the ability to better suppress undesired surface wave coupling (with single sided operation), and the ability to increase the system's sensitivity to small flaws or grain size variation in metals.

While axicons are preferably used in the preferred embodiments, diffractive optical elements as well as holographic optical components can be used instead to emulate the function of an axicon. Computer generated diffractive optical elements can also be designed to accommodate systems with specific symmetries, beyond the circularly symmetric embodiment discussed herein. Other fixed optical elements may be used in place of the axicon used in the preferred embodiments, depending on the symmetry and shape of the workpiece and its acoustic properties (homogeneous, inhomogeneous), etc.

From the foregoing description, it will be apparent that the presently disclosed technology has a number of advantages, some of which have been described herein, and others of which are inherent in the embodiments described or claimed herein. Also, it will be understood that modifications can be made to the apparatus and method described herein without departing from the teachings of subject matter described herein. As such, the presently disclosed technology is not to be limited to the described embodiments except as required by the appended claims.

What is claimed is:

1. An ultrasonic inspection system comprising:
   a laser generator for impinging a workpiece with light for generating a thermo-elastic acoustic reaction in a workpiece;
   a probe laser for impinging the workpiece with an annularly-shaped probe light for interaction with the acoustic signal in the workpiece resulting in a modulated return beam; and
   a photodetector having a sensitive region for detecting an annularly-shaped fringe pattern generated by an interaction of a reference signal with the modulated return beam at said sensitive region.

2. The ultrasonic inspection system of claim 1 including an axicon for receiving-light from the probe laser and forming the annularly-shaped probe light which impinges the workpiece, said axicon receiving modulated return light from the workpiece.

3. The ultrasonic inspection system of claim 2 wherein the light produced by the laser generator transits another axicon before impinging said workpiece whereby the light impinging said workpiece is annularly-shaped.

4. The ultrasonic inspection system of claim 3 wherein the photo detector has a pair of electrodes, one of the electrodes being disposed parallel to a first edge of the photo detector and the other one of the electrodes being disposed parallel to a second edge of the photodetector, the sensitive region being disposed between the pair of electrodes.

5. The ultrasonic inspection system of claim 4 further including a beam splitter disposed between the probe laser and the axicon for splitting off a reference beam, an axis of said reference beam being directed to the photodetector at a non-perpendicular angle to a major surface of the sensitive region of the photodetector.

6. The ultrasonic inspection system of claim 2 wherein the photodetector has a pair of electrodes, one of the electrodes surrounding the annularly shaped fringe pattern and another electrode being disposed within the annularly shaped fringe pattern.

7. The ultrasonic inspection system of claim 6 including a beam splitter disposed between the probe laser and the axicon for splitting off a reference beam which is directed to the photodetector.

8. The ultrasonic inspection system of claim 7 including a mirrored surface for reflecting the reference beam through the splitter to the photo detector.

9. The ultrasonic inspection system of claim 8 further including a modified axicon for diverging the modulated return beam and reference beam toward the sensitive region of the photo detector at different angles.

10. The ultrasonic inspection system of claim 9 wherein the light produced by the laser generator impinges one surface of said workpiece and the annularly-shaped probe light impinges a different surface of said workpiece.

11. The ultrasonic inspection system of claim 10 wherein said one surface of said workpiece is disposed parallel to said different surface of said workpiece.

12. The ultrasonic inspection system of claim 1 wherein the photo detector has a pair of electrodes, one of the electrodes being disposed parallel to a first edge of the photodetector and the other one of the electrodes being disposed parallel to a second edge of the photodetector, the sensitive region being disposed between the pair of electrodes.

13. The ultrasonic inspection system of claim 12 including an axicon for receiving light from the probe laser and forming the annularly-shaped probe light which impinges the workpiece, said axicon receiving modulated return light from the workpiece.

14. The ultrasonic inspection system of claim 13 further including a beam splitter disposed between the probe laser and the axicon for splitting off a reference beam, an axis of said reference beam being directed to the photo detector at a non-perpendicular angle to a major surface of the sensitive region of the photodetector.

15. The ultrasonic inspection system of claim 1 wherein the annularly-shaped fringe pattern covers only a portion of the sensitive region.

16. The ultrasonic inspection system of claim 1 wherein a portion of the workpiece being impinged by the light of the laser generator is less than a portion of the workpiece being impinged by the light of the probe laser.

17. A method for inspecting a workpiece comprising:
   generating a thermo-elastic acoustic signal in said workpiece;
   optically sampling said thermo-elastic acoustic signal using an annularly-shaped probe beam;
   generating a reference signal; and
   generating a fringe pattern based on an interaction between said reference signal and said optically sampled thermo-elastic acoustic signal.

18. The method of claim 17 wherein the thermo-elastic acoustic signal is generated in said workpiece around a spot of light directed to said workpiece.

19. The method of claim 18 wherein the annularly-shaped probe beam is centered on said spot of light.

20. The method of claim 17 wherein the fringe pattern is annularly-shaped and wherein the single detector has a pair of electrodes, one of the electrodes surrounding the annularly shaped fringe pattern and another electrode being disposed within the annularly shaped fringe pattern.

21. The method of claim 20 wherein the annularly-shaped probe beam is formed by an axicon, wherein the axicon collects the optically sampled thermo-elastic acoustic signal and wherein a beam splitter directs the optically sampled thermo-elastic acoustic signal collected by the axicon toward a modified axicon.

22. The method of claim 21 wherein light of the annularly-shaped probe beam and the light of the reference beam is produced by a probe laser.

23. The method of claim 17 wherein the fringe pattern is annularly shaped and wherein the single detector has a pair of electrodes, one of the electrodes being disposed parallel to a first edge of the photodetector and the other one of the electrodes being disposed parallel to a second edge of the photo detector, the sensitive region being disposed between the pair of electrodes.

24. The method of claim 17 wherein the thermo-elastic acoustic signal is generated in said workpiece in response to an annular ring of light directed to said workpiece by a laser generator in cooperation with an axicon, the thermo-elastic acoustic signal comprising a central spot surrounded by an annular region.

25. The method of claim 24 wherein the annularly-shaped probe beam includes a centrally disposed spot probe in an annularly-shaped portion of the annularly-shaped probe beam, the annularly-shaped portion of the annularly-shaped probe beam being aligned with the annular region of the thermo-elastic acoustic signal and the centrally disposed spot probe being aligned with the central spot of the thermo-elastic acoustic signal.

26. The method of claim 17 wherein the fringe pattern covers only a portion of a surface of the single detector.

* * * * *

UNITED STATES PATENT AND TRADEMARK OFFICE
CERTIFICATE OF CORRECTION

PATENT NO. : 7,262,861 B1 Page 1 of 1
APPLICATION NO. : 10/852782
DATED : August 28, 2007
INVENTOR(S) : David M. Pepper et al.

It is certified that error appears in the above-identified patent and that said Letters Patent is hereby corrected as shown below:

Title Page, Item (76)
The name of the Assignee is incorrectly spelled. Please correct the name of the Assignee to:

HRL LABORATORIES, LLC

Signed and Sealed this

Twentieth Day of November, 2007

JON W. DUDAS
*Director of the United States Patent and Trademark Office*